United States Patent
Misra et al.

[11] Patent Number: 6,107,305
[45] Date of Patent: Aug. 22, 2000

[54] USE OF PYRAZOLO [3,4-B] PYRIDINE AS CYCLIN DEPENDENT KINASE INHIBITORS

[75] Inventors: Raj N. Misra, Hopewell; S. David Kimball, East Windsor, both of N.J.; David B. Rawlins, Morrisville; Kevin R. Webster, Yardley, both of Pa.; Isia Bursuker, Cheshire, Conn.

[73] Assignee: Bristol-Myers Squibb Company, Princeton, N.J.

[21] Appl. No.: 09/209,575

[22] Filed: Dec. 11, 1998

Related U.S. Application Data

[60] Provisional application No. 60/069,633, Dec. 13, 1997.

[51] Int. Cl.⁷ .................... A61K 31/435; C07D 471/04
[52] U.S. Cl. ................................... 514/303; 546/120
[58] Field of Search ............................ 546/120; 514/303

[56] References Cited

U.S. PATENT DOCUMENTS

| | | | |
|---|---|---|---|
| 3,755,340 | 8/1973 | Hoehn et al. | 546/120 |
| 3,773,778 | 11/1973 | Hoehn et al. | 546/120 |
| 3,810,905 | 5/1974 | Hoehn et al. | 546/120 |
| 3,985,757 | 10/1976 | Denzel et al. | 546/120 |
| 3,987,051 | 10/1976 | Denzel et al. | 546/120 |
| 4,552,883 | 11/1985 | Bare et al. | 546/120 |
| 5,733,920 | 3/1998 | Mansuri et al. | 514/337 |

OTHER PUBLICATIONS

Höhn et al., "1H–Pyrazolo[3,4–b] pyridines", J. Heterocyclic Chem., vol. 9, pp. 235–253 (1972).

*Primary Examiner*—Bernard Dentz
*Attorney, Agent, or Firm*—Timothy J. Babcock

[57] ABSTRACT

Compounds of the formula

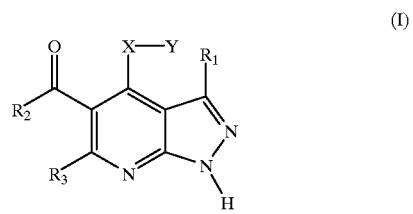

and pharmaceutically acceptable salts thereof for use as inhibitors of cyclin dependent kinases, wherein:

X is O, $S(O)_m$;

Y is alkyl, aryl, arylalkyl, heteroaryl, heteroarylalkyl, cycloalkyl, cycloalkylalkyl, heterocycloalkyl, heterocycloalkylalkyl;

$R_1$ is hydrogen or lower alkyl;

$R_2$ is alkyl, aryl, arylalkyl, heteroaryl, heteroarylalkyl, cycloalkyl, cycloalkylalkyl, heterocycloalkyl, heterocycloalkylalkyl, —O-alkyl, —O-aryl, —$NR_4R_5$;

$R_3$ is hydrogen or lower alkyl;

$R_4$ is hydrogen, alkyl, aryl, arylalkyl, heteroaryl, heteroarylalkyl, cycloalkyl, cycloalkylalkyl, heterocycloalkyl, heterocycloalkylalkyl, —O-alkyl, —O-aryl;

$R_5$ is hydrogen, alkyl, aryl, alkylaryl, heteroaryl, alkylheteroaryl, cycloalkyl, alkylcycloalkyl, heterocycloalkyl, alkylheterocycloalkyl, —O-alkyl, —O-aryl; and m is 0, 1 or 2.

The compounds of formula I are protein kinase inhibitors and are useful in the treatment and prevention of proliferative diseases, for example, cancer, inflammation and arthritis. They may also be useful in the treatment of neurodegenerative diseases such as Alzheimer's disease, cardiovascular diseases, viral diseases and fungal diseases.

26 Claims, No Drawings

USE OF PYRAZOLO [3,4-B] PYRIDINE AS CYCLIN DEPENDENT KINASE INHIBITORS

This application claims priority benefit under Title 35 § 119(e) of United States Provisional Application Ser. No. 60/069,633, filed Dec. 13, 1997 having the same title, the entire contents of which are incorporated herein by reference.

BRIEF DESCRIPTION OF THE INVENTION

The present invention is directed to the use of compounds of the formula

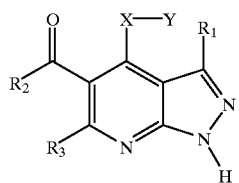

and pharmaceutically acceptable salts thereof as inhibitors of cyclin dependent kinases. As used in formula I, and throughout the specification, the symbols have the following meanings:

$X$ is O, $S(O)_m$;

$Y$ is alkyl, aryl, arylalkyl, heteroaryl, heteroarylalkyl, cycloalkyl, cycloalkylalkyl, heterocycloalkyl, heterocycloalkylalkyl;

$R_1$ is hydrogen or lower alkyl;

$R_2$ is alkyl, aryl, arylalkyl, heteroaryl, heteroarylalkyl, cycloalkyl, cycloalkylalkyl, heterocycloalkyl, heterocycloalkylalkyl, —O-alkyl, —O-aryl, —NR$_4$R$_5$;

$R_3$ is hydrogen or lower alkyl;

$R_4$ is hydrogen, alkyl, aryl, arylalkyl, heteroaryl, heteroarylalkyl, cycloalkyl, cycloalkylalkyl, heterocycloalkyl, heterocycloalkylalkyl, —O-alkyl, —O-aryl;

$R_5$ is hydrogen, alkyl, aryl, alkylaryl, heteroaryl, alkylheteroaryl, cycloalkyl, alkylcycloalkyl, heterocycloalkyl, alkylheterocycloalkyl, —O-alkyl, —O-aryl; and $m$ is 0, 1 or 2.

The compounds of formula I are protein kinase inhibitors and are useful in the treatment and prevention of proliferative diseases, for example, cancer, inflammation and arthritis. They may also be useful in the treatment of neurodegenerative diseases such Alzheimer's disease, cardiovascular diseases, viral diseases and fungal diseases.

DESCRIPTION OF THE INVENTION

The present invention provides for a method of using compounds of formula I as inhibitors of cyclin dependent kinases, which are active in the treatment of proliferative diseases, such as for example, but not limited to, cancer, Alzheimer's disease, arthritis, inflammation, and cardiovascular disease. The present invention also contemplates pharmaceutical compositions employing such compounds.

Listed below are definitions of various terms used to describe the compounds of the instant invention. These definitions apply to the terms as they are used throughout the specification (unless they are otherwise limited in specific instances) either individually or as part of a larger group.

It should be noted that any heteroatom with unsatisfied valances is assumed to have the hydrogen atom to satisfy the valances.

Carboxylate anion refers to a negatively charged group —COO$^-$.

The term "alkyl" or "alk" refers to a monovalent alkane (hydrocarbon) derived radical containing from 1 to 12 carbon atoms unless otherwise defined. The term "lower alkyl" refers to an alkyl group of 1 to 6 carbon atoms. An alkyl group is an optionally substituted straight, branched or cyclic saturated hydrocarbon group. When substituted, alkyl groups may be substituted with up to four substituent groups, R as defined, at any available point of attachment. When the alkyl group is said to be substituted with an alkyl group, this is used interchangeably with "branched alkyl group". Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents may include but are not limited to one or more of the following groups: halo (such as F, Cl, Br, I), haloalkyl (such as CCl$_3$ or CF$_3$), alkoxy, aryloxy, alkyl $S(O)_m$ (m=0, 1, 2), aryl $S(O)_m$ (m=0, 1, 2) hydroxy, carboxy (—COOH), alkyloxycarbonyl (—COOR'), alkylcarbonyloxy (—OCOR'), amino (—NH$_2$), quaternary nitrogen, carbamoyl (—NHCOOR'— or —OCONHR'—), urea (—NHCONHR'—), thiol (—SH), cyano or nitro. Alkyl groups as defined may also comprise one or more carbon to carbon double bonds or one or more carbon to carbon triple bonds.

The term "alkenyl" refers to a hydrocarbon radical straight, branched or cyclic containing from 2 to 12 carbon atoms and at least one carbon to carbon double bond.

The term "alkynyl" refers to a hydrocarbon radical straight, branched or cyclic containing from 2 to 12 carbon atoms and at least one carbon to carbon triple bond.

Cycloalkyl is a type of alkyl containing from 3 to 15 carbon atom, without alternating or resonating double bonds between carbon atoms. It may contain from 1 to 4 rings. Exemplary unsubstituted such groups include cyclopropyl, cyclobutyl, cyclopentyl, cyclohexyl, etc. Exemplary substituents include one or more of the following groups: halogen, alkyl, alkoxy, alkyl, hydroxy, amino, nitro, cyano, thiol and/or alkylthio.

The terms "alkoxy" or "alkylthio", as used herein, denote an alkyl group as described above bonded through an oxygen linkage (—O—) or a sulfur linkage (—S—), respectively.

The term "alkyloxycarbonyl", as used herein, denotes an alkoxy group bonded through a carbonyl group. An alkoxycarbonyl radical is represented by the formula: —C(O)OR, where the R group is a straight or branched $C_{1-6}$ alkyl group.

The term "alkylcarbonyl" refers to an alkyl group bonded through a carbonyl group.

The term "alkylcarbonyloxy", as used herein, denotes an alkylcarbonyl group which is bonded through an oxygen linkage.

The term "arylalkyl", as used herein, denotes an aromatic ring bonded through an alkyl group as described above.

The term "aryl" refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more groups including, but not limited to halogen, alkyl, alkoxy, hydroxy, carboxy, carbamoyl, alkyloxycarbonyl, nitro, trifluoromethyl, amino, cycloalkyl, cyano, alkylS(O)$_m$ (m=0, 1, 2), or thiol.

The term "heteroaryl" refers to a monocyclic aromatic hydrocarbon group having 5 or 6 ring atoms, or a bicyclic aromatic group having 8 to 10 atoms, containing at least one heteroatom, O, S, or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Additional nitrogen atoms may be present together with the first nitrogen and oxygen or sulfur. Exemplary heteroaryl groups include the following: thienyl, furyl, pyrrolyl, pyridinyl, imidazolyl, pyrrolidinyl, piperidinyl, thiazolyl, oxazolyl, triazolyl, pyrazolyl, isoxazolyl, isothiazolyl, pyrazinyl, pyridazinyl, pyrimidinal, triazinylazepinyl, indolyl, isoindolyl, quinolinyl, isoquinolinyl, benzothiazolyl, benzoxazolyl, benzimidazolyl, benzoxadiazolyl, benzofurazanyl and tetrahydropyranyl. Exemplary substituents include one or more of the following: halo, alkyl, alkoxy, hydroxy, cycloalkyl, nitro, cyano, amino, alkylS(O)$_m$ (m=0, 1, 2), or thiol. The term "heteroarylalkyl", as used herein denotes a heteroaryl ring bonded through an alkyl group as described hereinabove.

The term "heteroarylium" refers to heteroaryl groups bearing a quaternary nitrogen atom and thus a positive charge.

The term "heterocycloalkyl" refers to a cycloalkyl group (nonaromatic) in which one of the carbon atoms in the ring is replaced by a heteroatom selected from O, S or N, and in which up to three additional carbon atoms may be replaced by said heteroatoms. In addition, the sulfur may be oxidated to the sulfone (—SO$_2$—) or sulfoxide (—SO—) and the nitrogen may be quaternary.

The term "quaternary nitrogen" refers to a tetravalent positively charged nitrogen atom including, e.g. the positively charged nitrogen in a tetraalkylammonium group (e.g. tetramethylammonium, N-methylpyridinium), the positively charged nitrogen in protonated ammonium species (e.g. trimethylhydroammonium, N-hydropyridinium), the positively charged nitrogen in amine N-oxides (e.g. N-methyl-morpholine-N-oxide, pyridine —N-oxide), and the positively charged nitrogen in an N-amino-ammonium group (e.g. N-aminopyridinium).

The term "heteroatom" means O, S, P or N, selected on an independent basis.

The term "halogen" or "halo" refers to chlorine, bromine, fluorine, iodine.

The term "PMB" refers to para-methoxybenzyl.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al., *Protective Groups in Organic Synthesis,* Wiley, N.Y. (1991).

Suitable examples of salts of the compounds according to the invention with inorganic or organic acids are hydrochloride, hydrobromide, sulfate, phosphate. Salts which are unsuitable for pharmaceutical uses but which can be employed, for example, for the isolation or purification of free compounds I or their pharmaceutically acceptable salts, are also included.

All stereoisomers of the compounds of the instant invention are contemplated, either in admixture or in pure or substantially pure form. The definition of the compounds according to the invention embraces all possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates by conventional methods, such as, for example, salt formation with an optically active acid followed by crystallization.

It should be understood that the present invention includes prodrug forms of the compounds of formula I. Various forms of prodrugs are well known in the art. For examples of such prodrug derivatives, see:

(a) *Design of Prodrugs,* edited by H. Bundgaard (Elsevier, 1985); and *Methods in Enzymology,* Vol. 42, pp. 309–396, edited by K. Widder et al., (Academic Press, 1985);

(b) *A Textbook of Drug Design and Development,* edited by Krosgaard-Larsen and H. Bundgaard, Chapter 5, "Design and Application of Prodrugs," by H. Bundgaard, pp. 113–191 (1991);

(c) H. Bundgaard, *Advanced Drug Deliver Reviews,* 8, pp. 1–38 (1992);

(d) H. Bundgaard et al., *Journal of Pharmaceutical Sciences,* 77, 285 (1988); and (e) N. Kayeka et al., *Chem. Phar. Bull.,* 32, 692 (1984).

It should be understood that solvates (e.g. hydrates) of the compounds of formula I are also within the scope of the present invention. Methods of salvation are generally known in the art. Accordingly, the compounds of the instant invention may be in the free or hydrate form, and may be obtained by methods exemplified by the following schemes.

Compounds of formula I for use as inhibitors of cyclin dependent kinases can be prepared by reacting a compound of formula

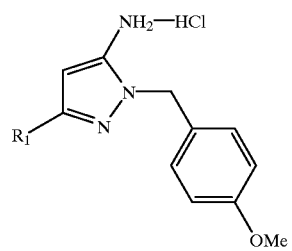

(II)

with a base such as sodium hydroxide or sodium carbonate to give a free base of formula

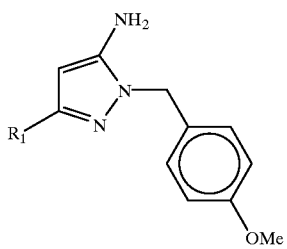

(IIa)

Compound IIa is reacted with a compound of formula

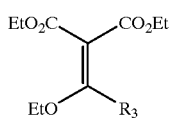

(III)

at 130° under reduced pressure to obtain compounds of formula

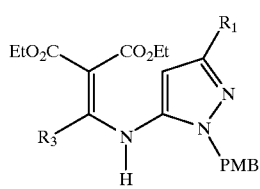

(IV)

The starting compound of formula II, where $R_1$ is hydrogen is easily prepared by reacting acrylonitrile with hydrazine hydrate in a solvent such as THF, followed by addition of p-methoxybenzaldehyde. The compound which results from this reaction is then reacted with a mixture of sodium n-butoxide in n-butanol followed by HCl to provide the key early intermediate of compound II.

Compounds of formula IV are then reacted at a temperature from 220° to 260° in diphenyl ether to obtain a compound of formula

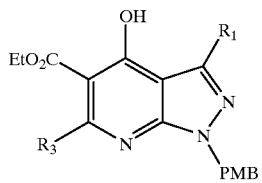

(V)

Compound V is then reacted with phosphorous oxychloride at a temperature from 25° to 130° to yield a compound of formula

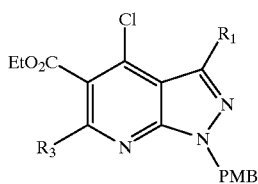

(VI)

Compound VI is reacted with an alkoxide such as sodium n-butoxide in n-butanol at a temperature from 25° to 90°, and then water is added to form a compound of formula

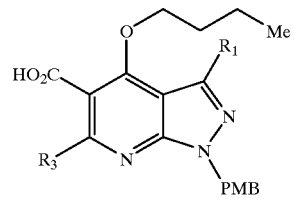

(VII)

wherein an n-butoxy group is added to the 4 carbon, such that X of formula I is oxygen and Y is an n-butyl lower alkyl group.

Compound VII is then reacted with a mixture of oxalyl chloride and catalytic DMF in an inert solvent such as dichloromethane followed by N,O-dimethylhydroxylamine hydrochloride and an amine base, such as triethylamine, to provide compounds of formula

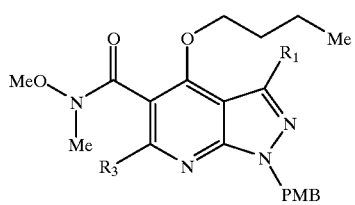

(VIII)

Compounds of formula VIII are then reacted with an acid, such as trifluoroacetic acid (TFA), at a temperature from 25° to 90°, or hydrogen in the presence of a catalyst, such as palladium on carbon, to provide compounds of formula

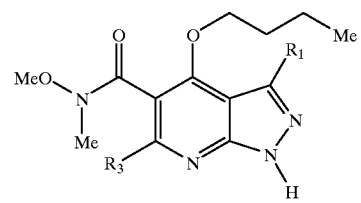

(IX)

Compounds of formula IX are then reacted with an excess of an organometallic reagent such as an organolithium (2–15 eq) in THF or ether to provide compounds of formula I where X is oxygen and $R_2$ is alkyl or aryl.

Compound VII may alternatively be reacted with a chlorinating agent, such as oxalyl chloride, and catalytic DMF in an inert solvent such as dichloromethane to afford compounds of the formula

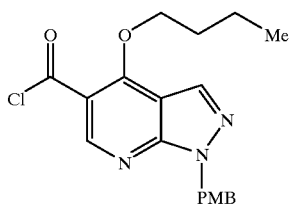
(X)

Compounds of formula X are then reacted with an organometallic reagent such as an organolithium (0.70–1.5 eq.) in THF or ether at a temperature from −90° to −20° to give compounds of the formula

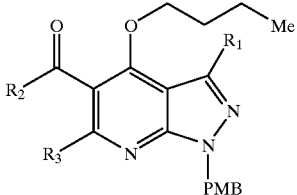
(XI)

Compounds of the formula XI are then reacted with an acid, such as TFA, or hydrogen in the presence of a catalyst, such as palladium on carbon to give compounds of formula I where X is oxygen and $R_2$ is not —O-alkyl, —O-aryl, or —$NR_4R_5$.

In another alternative scheme, compound VII may be reacted with oxalyl chloride and catalytic DMF followed by $R_4R_5NH$ and triethylamine in an inert solvent such as dichloromethane to provide the compound of formula

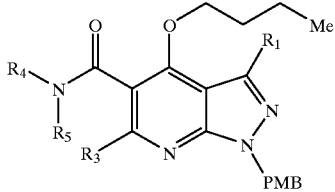
(XII)

Compound XII is then reacted with TFA at a temperature from 25° to 90° to obtain compounds of the formula

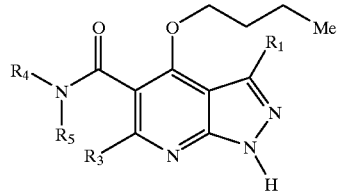
(XIII)

An alternative synthesis of compounds of formula I where $R_2$ is aryl or heteroaryl is exemplified by compound XIV below, where in formula I $R_1$ is hydrogen, $R_2$ is phenyl, and $R_3$ is hydrogen.

A compound of formula XIV

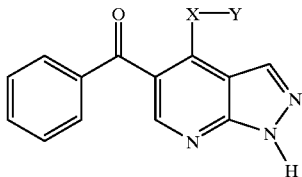
(XIV)

may be prepared by reacting compound IIa with a compound of the formula (XV)

[structure]

to provide compounds of the formula (XVI)

[structure]

Compound XV may be prepared by reacting ethylbenzoyl acetate with triethylorthoformate in a solution of acetic anhydride at a temperature from 100 to 145°.

The compound of formula XVI is then added to diphenyl ether heated to a temperature form 220° to 260° to provide a compound of the formula

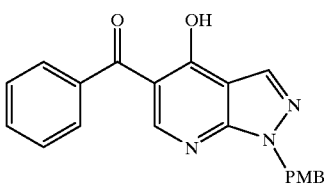
(XVII)

Compound XVII is then reacted with phosphorous oxychloride at a temperature from 25° to 130° to provide a compound of the formula

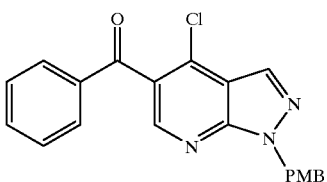
(XVIII)

which is then reacted with a Y—XNa such that the nucleophilic X is substituted for the chlorine on the 4 carbon to provide compounds of the formula (XIX)

wherein X is oxygen or sulfur. Reaction in TFA at a temperature from 25° to 90° removes the PMB-protecting group to provide compound XIV, when Y is not CH$_2$Ph.

Alternatively, reacting compound XIV, when X is oxygen or sulfur and Y is hydrogen, with benzylbromide in the presence of sodium bicarbonate results in the addition of a benzyl group to X.

Compounds of formula XIV, where X is sulfoxide or sulfone may be prepared from compound of formula (XX)

according to the following reaction schemes:

Intermediates of this invention may also be prepared by processes disclosed in U.S. Pat. Nos. 3,828,057, 3,966,746, 3,979,399, and 3,985,757 which are incorporated by reference herein. More specifically, intermediates of formula II may be prepared by procedures described in Hoehn, H., Z. Chem. 10, pp. 386–388 (1970). Intermediates of formula I, where X is oxygen and Y is hydrogen may be prepared as described in Denzel, T., and Hoehn, H. Arch. Chem. 309, pp. 486–503 (1976).

Compounds of formula II and III are commercially available or may be prepared by methods known to one of ordinary skill in the art.

All other compounds may be prepared by modification of the procedures described herein.

The preferred compounds of formula I are those where:
R$_1$ is hydrogen;
R$_2$ is aryl or heteroaryl;
R$_3$ is hydrogen;
X is oxygen; and
Y is alkyl, cycloalkyl or cycloalkylalkyl;

The most preferred compounds of formula I are those where:
R$_1$ is hydrogen;
R$_2$ is 4-bromo-2,6-difluorophenyl, 4-chloro-2,6-difluorophenyl, or 2,4,6-trifluorophenyl;
R$_3$ is hydrogen;
X is oxygen; and
Y is lower alkyl.

The compounds according to the invention have pharmacological properties; in particular, the compounds of formula I are inhibitors of protein kinases such as the cyclin dependent kinases (cdks), for example, cdc2 (cdk1), cdk2, and cdk4. The novel compounds of formula I are expected to be useful in the therapy of proliferative diseases such as cancer, autoimmune diseases, viral diseases, fungal diseases, neurodegenerative disorders and cardiovascular disease.

More specifically, the compounds of formula I are useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Due to the key role of cdks in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of formula I may also be useful in the treatment of Alzheimer's disease, as suggested by the recent finding that cdk5 is involved in the phosphorylation of tau protein (J. Biochem, 117, 741–749 (1995)).

Compounds of formula I may induce or inhibit apoptosis. The apoptotic response is aberrant in a variety of human diseases. Compounds of formula I, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of formula I, as inhibitors of the cdks, can modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of formula I may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of formula I may also be useful in inhibiting tumor angiogenesis and metastasis.

Compounds of formula I may also act as inhibitors of other protein kinases, e.g., protein kinase C, her2, raf 1, MEK1, MAP kinase, EGF receptor, PDGF receptor, IGF receptor, PI3 kinase, wee1 kinase, Src, Abl and thus be effective in the treatment of diseases associated with other protein kinases.

The compounds of this invention may also be useful in combination (administered together or sequentially) with known anti-cancer treatments such as radiation therapy or with cytostatic or cytotoxic agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones; hormonal agents, such as tamoxifen; thymidilate synthase inhibitors, such as 5-fluorouracil; and anti-metabolites, such as methoxtrexate.

If formulated as a fixed dose, such combination products employ the compounds of this invention within the dosage range described below and the other pharmaceutically active agent or treatment within its approved dosage range. For example, the cdc2 inhibitor olomucine has been found to act synergistically with known cytotoxic agents in inducing apoptosis (J. Cell Sci., 108, 2897 (1995)). Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent. For example, the cytotoxic activity of the cyclin-dependent kinase inhibitor flavopiridol is affected by the sequence of administration with anticancer agents. Cancer Research, 57, 3375 (1997).

The pharmacological properties of the compounds of this invention may be confirmed by a number of pharmacological assays. The exemplified pharmacological assays which follow have been carried out with the compounds according to the invention and their salts. The compounds of examples 1 to 8 exhibited cdc2/cyclin B1 kinase activity with $IC_{50}$ values less than 50 $\mu$M. The compounds of examples 1 to 8 exhibited cdk2/cyclin E kinase activity with $IC_{50}$ values less than 50 $\mu$M. The compounds of examples 1 to 8 exhibited cdk4/cyclin D1 kinase activity with $IC_{50}$ values less than 50 $\mu$M.

cdc2/cyclin B1 Kinase Assay

The activity of cdc2/cyclin B 1 kinase was determined by monitoring the incorporation of $^{32}P$ into histone HI. The reaction consisted of 50 ng baculovirus expressed GST-cdc2, 75 ng baculovirus expressed GST-cyclin B1, 1 $\mu$g histone HI (Boehringer Mannheim), 0.2 mCi of $^{32}P$ g-ATP and 25 mM ATP in kinase buffer (50 mM Tris, pH 8.0, 10 mM $MgCl_2$, 1 mM EGTA, 0.5 mM DTT). The reaction was incubated at 30° C. for 30 minutes and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter (Marshak, D. R., Vanderberg, M. T., Bae, Y. S., Yu, I. J., J. of Cellular Biochemistry, 45, 391–400 (1991), incorporated by reference herein).

cdk2/cyclin E Kinase Assay

The activity of cdk2/cyclin E kinase was determined by monitoring the incorporation of $^{32}P$ into the retinoblastoma protein. The reaction consisted of 2.5 ng baculovirus expressed GST-cdk2/cyclin E, 500 ng bacterially produced GST-retinoblastoma protein (aa 776–928), 0.2 mCi $^{32}P$ g-ATP and 25 mM ATP in kinase buffer (50 mM Hepes, pH 8.0, 10 mM $MgCl_2$, 5 mM EGTA, 2 mM DTT). The reaction was incubated at 30° C. for 30 minutes and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter.

cdk 4/cyclin D1 Kinase Activity

The activity of cdk4/cyclin D1 kinase was determined by monitoring the incorporation of $^{32}P$ in to the retinoblastoma protein. The reaction consisted of 165 ng baculovirus expressed as GST-cdk4, 282 ng bacterially expressed as S-tag cyclin D1, 500 ng bacterially produced GST-retinoblastoma protein (aa 776–928), 0.2 $\mu$Ci $^{32}$P$\gamma$-ATP and 25 $\mu$M ATP in kinase buffer (50 mM Hepes, pH 8.0, 10 mM MgCl$_2$, 5 mM EGTA, 2 mM DTT). The reaction was incubated at 30° C. for 1 hour and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter (Coleman, K. G., Wautlet, B. S., Morissey, D, Mulheron, J. G., Sedman, S., Brinkley, P., Price, S., Wedster, K. R. (1997) Identification of CDK4 Sequences involved in cyclin D, and p16 binding. *J. Biol. Chem.* 272, 30:18869–18874, incorporated by reference herein).

Further subject matter of the invention also includes pharmaceuticals for use as described above including controlling cancer, inflammation and arthritis, which contain at least one compound of the formula I as defined above or at least one of its pharmacologically acceptable acid addition salts, and the use of a compound of the formula I as defined above for the preparation of a pharmaceutical having activity against proliferative diseases as described previously including against cancer, inflammation and/or arthritis.

The following examples and preparations describe the manner and process of making and using the invention and are illustrative rather than limiting. It should be understood that there may be many other embodiments which fall within the spirit and scope of the invention as defined by the claims appended hereto.

EXAMPLE 1

(4-Butoxy-1H-pyrazolo[3,4-b]pyridin-5-yl)(2,4,6-trifluorophenyl)methanone

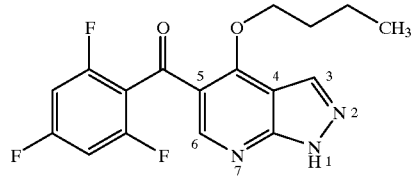

A. 1-[(4-Methoxyphenyl)methyl]-1H-pyrazol-5-amine

To a stirred mixture of 188 g (0.77 mols) of 1-[(4-Methoxyphenyl) methyl]-1H-pyrazol-5-amine hydrochloride in 2 L of methyl t-butyl ether (MTBE) and 1 L of water was added 0.76 L of 1N aq sodium hydroxide solution, the solids dissolved. The aqueous layer was separated and extracted with 1 L of MTBE. The organic layers were combined, washed with 0.5 L of brine, dried (sodium sulfate) and concentrated in vacuo to afford 132 g (84%) of compound A as a waxy orange-yellow powder.

B. [[[1-[(4-Methoxyphenyl)methyl]-1H-pyrazol-5-yl]amino]methylene]propanedioic acid diethyl ester A mixture of 126 g (0.62 mols) of Part A amine and 140 mL (0.69 mols) of diethyl ethoxymethylenemalonate was heated under reduced pressure with stirring to ~130° under a Dean-Stark apparatus. The reaction mixture was heated for 2.5 h then cooled to room temperature to give 237 g (100%) of compound B as an orange-red oil.

C. 4-Hydroxy-1-[(4-methoxyphenyl)methyl]-1H-pyrazolo[3,4-b]pyridine-5-carboxylic acid ethyl ester In a 2 L flask, fitted with a distillation head, 427 g of diphenyl ether was heated to ~235° under nitrogen. To the hot diphenyl ether solution was added a solution of 237 g of crude Part B compound in 250 mL of absolute ethanol over 1 h. The volatile materials (~90 to 120°) were collected through the distillation head while maintaining the pot temperature at ~230°. After 1 h the reaction mixture was cooled to ~45° and 350 mL of methanol was introduced. A thick suspension formed and was allowed to cool to room temperature with mechanical stirring. The resulting mixture was filtered and the solid washed with two-100 mL portions of methanol then 100 mL of heptane. The solid material was allowed to air-dry to afford 122 g (59%) of Part C compound as a fine pale orange powder.

D. 4-Chloro-1-[(4-methoxyphenyl)methyl]-1H-pyrazolo[3,4-b]pyridine-5-carboxylic acid ethyl ester A mixture of 88.6 g (0.27 mols) of Part C compound in 90 mL of phosphorous oxychloride was heated to ~115° for 50 minutes. The reaction mixture was cooled to room temperature, diluted with 900 mL of dichloromethane then carefully poured onto ~2 kg of crushed ice with stirring. The mixture was diluted with 1 L of dichloromethane and 1 L of water. The aqueous layer was separated and extracted with two-500 mL portions of dichloromethane. The organic layers were combined, dried (sodium sulfate) then filtered through a silica gel plug (~90 g, Merck flash silica) washing with an additional 500 mL of dichloromethane. The filtrate was concentrated in vacuo to give 81 g of crude material as a yellow solid. The solid was purified by flash chromatography (Merck silica, ~300 g, 3:1 to 1:1 heptane/ethyl acetate) to afford 61.7 g (66%) of Part D compound as a fine white powder.

E. 4Butoxy-1-[(4-methoxyphenyl)methyl]-1H-pyrazolo[3,4-b]pyridine-5-carboxylic acid To 100 mL (1.1 mols) of 1-butanol was added 1.1 g (48 mmol) of sodium metal piece by piece. The resultant mixture was heated until the sodium was dissolved completely to afford a sodium n-butoxide solution. To the above solution was added a solution of 5.13 g (14.8 mmol) of Part D compound in 100 mL of THF (distilled from ketyl) at room temperature over 20 minutes. The resultant suspension was well stirred at room temperature for 0.5 h and at 60–65° for 3 h. After this time, 0.5 mL (28 mmol) of water was added and the mixture was stirred at 60–65° C. for another 3 h. The resultant suspension was concentrated in vacuo, acidified with ca 150 mL of 5% aqueous potassium hydrogen sulfate solution to pH =1 and extracted with three-100 mL portions of methylene chloride. The combined organic extracts were dried (sodium sulfate) and concentrated in vacuo to give 5.30 g (100%) of crude Part E as a yellow solid.

F. 4-Butoxy-N-methoxy-1-[(4-methoxyphenyl)methyl]—N-methyl-1H-pyrazolo[3,4b]pyridine-5-carboxaiide To a suspension of 3.0 g (8.4 mmol) of Part E compound in 75 mL of dry methylene chloride was added 4 drops of DMF and 5.1 mL (2 M solution in methylene chloride, 10 mmol) of oxalyl chloride solution dropwise at room temperature. Gas was evolved during the addition. The resultant solution was stirred at room temperature for 0.5 h and concentrated in vacuo. The residue was dissolved in methylene chloride and concentrated in vacuo again to afford the acid chloride. To a mixture of the acid chloride and 990 mg (10 mmol) of N,O-dimethylhydroxylamine hydrochloride in 60 mL of methylene chloride was added 3.0 mL (22 mmol) of triethylamine dropwise at 0° with stirring. The mixture was stirred at room temperature for 1 h then saturated aqueous sodium bicarbonate solution was added until the solution was basic (pH was ca 8). The aqueous layer was separated and extracted with methylene chloride. The combined organic layers were dried (sodium sulfate), concentrated in vacuo and purified by flash chromatography (Merck silica, 50×200 mm, 1:1 EtOAc/hexanes and then EtOAc) to afford 3.1 g (93%) of Part F compound as a yellow solid.

G. 4-Butoxy-N-methoxy-N-methyl-1H-pyrazolo[3,4-b]pyridine-5-carboxamide

A solution of 1.7 g (4.3 mmol) of Part F compound in 13 mL of trifluoroacetic acid was stirred at 65° for 2.5 h then cooled, concentrated in vacuo and neutralized with saturated aqueous sodium bicarbonate solution. The precipitate which formed was collected by filtration, washed with water and then dried. The crude material was dissolved in EtOAc and precipitated by addition of hexanes to afford 1.1 g (89%) of Part G compound as a yellow solid.

H. (4-Butoxy-1H-pyrazolo[3,4-b]pyridin-5-yl)(2,4,6-trifiluorophenyl)methanone

To a solution of 2.1 mL (21 mmol) of 1,3,5-trifluorobenzene in 45 mL of THF (distilled from ketyl) was added 12.8 mL (1.6 M solution in hexanes, 20.5 mmol) of n-butyllithium solution dropwise at −78° under argon. The resultant solution was stirred at −78° for 0.5 h and at −45° for 10 minutes. The anion solution was cooled to −78°, then a solution 1.14 g (4.1 mmol) of Part G compound in 25 mL of THF was added dropwise at −78°. The resultant solution was stirred at −78° for 0.5 h and at 0° for 2 h. The reaction was quenched by adding 1 N aqueous hydrochloric acid at 0° C. and then neutralized with saturated aqueous sodium bicarbonate solution. The mixture was extracted with EtOAc. The combined extracts were dried (sodium sulfate) and concentrated in vacuo to give a solid. The crude solid was recrystallized (1:1 EtOAc/hexanes) to afford 0.94 g (66%) of the title compound as a yellowish solid, mp 209–211° C.

LC-MS: 350 (M+H)$^+$.

HPLC: $T_R$ (YMC 4.6×50 mm ODS S-3 MICRON; 2.5 mL/min, gradient 0–100% B over 8 minutes, Buffer A=MeOH/H$_2$O/H$_3$PO$_4$ (10:90:0.2), Buffer B=MeOH/H$_2$O/H$_3$PO$_4$ (90:10:0.2))=7.2 minutes, >99% of total peak area at 254 nM.

EXAMPLE 2

(4-Butoxy-1H-pyrazolo[3,4-b]pyridin-5-yl)(2,3,5,6-tetrafluoro4-methylphenyl)methanone

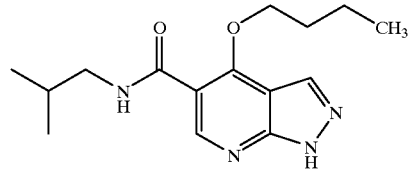

A. (4-Butoxy-1-[(4-methoxyphenyl)methyl]-1H-pyrazolo[3,4-b]pyridin-5-yl) (2,3,5,6-tetrafluoro4-methylphenyl)methanone To a mixture of 214 mg (0.60 mmol) of Example 1, Part E compound in 8 mL of dry methylene chloride at room temperature was added a small drop of DMF then 0.36 mL (2M mmol) of oxalyl cride, 0.72 mmol) of oxalyl chloride solution, gas evolution. After 30 minutes the reaction mixture was concentrated in vacuo then additional methylene chloride was added and concentrated again to afford the crude acid chloride. The crude acid chloride was dissolved in 3 mL of THF. A 0.75 mL portion of the acid chloride solution (~0.15 mmol) was removed and added at −78° to a solution of 4-methyl-2,3,5,6-tetrafluorophenyllithium (0.18 mmol, prepared from n-butyllithium and 1-bromo-4-methyl-2,3,5,6-tetrafluorobenzene in THF at −78°) in 1 mL of THF. The reaction mixture was stirred at −78° for 3 h then at room temperature overnight. The resulting solution was quenched with 1N aqueous HCl solution, neutralized with aqueous saturated sodium bicarbonate and extracted with EtOAc. The organic layer was dried (sodium sulfate) concentrated in vacuo and purified by flash chromatography (Merck silica, EtOAc/hexane) to give 22 mg (29%) of Part A compound.

B. (4-Butoxy-1H-pyrazolo[3,4-b]pyridin-5-yl)(2,3,5,6-tetrafluoro-4-methylphenyl)methanone A solution of 22 mg (0.044 mmol) of Part A compound in 1 mL of TFA was heated to 65° for 2.5 h. The reaction mixture was cooled, concentrated in vacuo then added was aqueous sodium bicarbonate. The solid which formed was washed with water, dried under vacuum and recrystallized (EtOAc) to give 5 mg (29%) of the title compound as a white solid.

LC-MS: 382 (M+H)$^+$.

HPLC: $T_R$ (Zorbax, SB-C18, 4.6×75 mm; 2.5 mL/min, gradient 0–100% B over 8 minutes, Buffer A=MeOH/H$_2$O/H$_3$PO$_4$ (10:90:0.2), Buffer B=MeOH/H$_2$O/H$_3$PO$_4$ (90:10:0.2))=8.4 minutes, >99% of total peak area at 254 nM.

EXAMPLE 3

4-Butoxy-N-(2-methylpropyl)-1H-pyrazolo[3,4-b]pyridine5-carboxamide

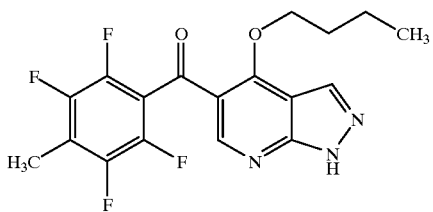

To a mixture of 1.00 g (2.8 mmol) of Example 1, Part E compound in 25 mL of dry methylene chloride at room temperature was added 2 small drops of DMF then 1.7 mL (2M in methylene chloride, 3.4 mmol) of oxalyl chloride solution, gas evolution. After 30 minutes the reaction mixture was concentrated in vacuo then additional methylene chloride was added and concentrated again to afford the crude acid chloride. The crude acid chloride was dissolved in 10 mL of dichloromethane. A 1 mL portion of the solution of the acid chloride (0.28mmol) was removed and added to a solution of 30 mg (0.40 mmol) of isobutylamine and 81 mg (0.80 mmol) of triethylamine in 1 mL of dichloromethane at 0°. The reaction mixture was warmed to room temperature over 1.5 h then ~1 mL of saturated aqueous sodium bicarbonate was added and extracted with two-1 mL portions of dichloromethane. The combined organic extracts were dried (sodium sulfate) and concentrated in vacuo to give a solid. The crude solid was dissolved in 3 mL of TFA and then heated to 65° for 2.5 h. The reaction mixture was cooled, concentrated in vacuo then partitioned between saturated aqueous sodium bicarbonate and dichloromethane. The organic phase was separated, dried (sodium sulfate) and concentrated in vacuo. The crude material was purified by flash chromatography (Merck silica, 1:19 MeOH/dichloromethane) to afford 71 mg (57%) of the title compound as a light brown solid.

LC-MS: 291 (M+H)$^+$.

HPLC: $T_R$ (Zorbax, SB-C18, 4.6×75 mm; 2.5 mL/min, gradient 0–100% B over 8 minutes, Buffer A=MeOH/H$_2$O/H$_3$PO$_4$ (10:90:0.2), Buffer B=MeOH/H$_2$O/H$_3$PO$_4$ (90:10:0.2))=7.2 minutes, 97% of total peak area at 254 nM.

EXAMPLE 4

[4-(Cyclohexylmethoxy)-1H-pyrazolo[3,4-b]pyridin-5-yl]phenylmethanone

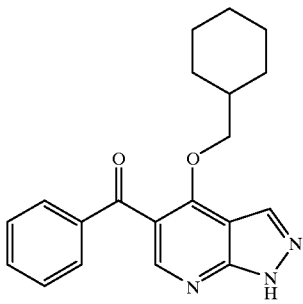

A. α-(Ethoxymethylene)-β-oxobenzenepropanoic acid ethyl ester

A solution of ethylbenzoyl acetate (50 mL, 0.29 mol), triethyl orthoformate (72 mL, 0.43 mol), and acetic anhydride (68 mL, 0.73 mol) was heated at 145° C. under nitrogen for 6 h. After removal of the resulting ethanol under low vacuum, the Part A compound (44%) was isolated by vacuum distillation (3 mm Hg, 165–169° C.) as a brown oil.

B. α-[[[1-[(4-Methoxyphenyl)methyl]1H-pyrazol-5-yl]amino]methylene]-β-oxobenzenepropanoic acid ethyl ester Example 1, Part A amine hydrochloride (5.0 g, 21 mmol) was suspended in ether (250 mL) and then 10% aqueous K$_2$CO$_3$ solution (200 mL) was added. The mixture was stirred at room temperature for 1.5 h and extracted with CH$_2$Cl$_2$ (2×250 mL). The combined organic layers were concentrated in vacuo to give the free amine as a brown oil. The amine was combined with Part A compound (5.3 g, 21 mmol) and heated neat at 120° C. for 1.5 h and then cooled to room temperature. The ethanol by-product was removed in vacuo to give Part B compound (9 g, 100%).

C. [(4-Cyclohexylmethoxy)-1-[(4-methoxyphenyl)methyl]-1H-pyrazolo[3,4-b]pyridin-5-yl]phenylmethanone Diphenyl ether (50 mL) was heated to 250° C. under nitrogen then a solution of Part B compound (7.0 g, 20 mmol) in 20 mL of diphenyl ether was added dropwise. The temperature was maintained for 1.5 h, after which the solution was cooled to room temperature. The diphenyl ether was removed by distillation (5 mmHg, 93° C.). The pot residue was added to hexane (40 mL) and a yellow precipitate formed. The solid was isolated by vacuum filtration and washed with methanol to give Part C compound (2.5 g, 40%) as a yellow grey solid.

D. (4-Chloro-1-[(4-methoxyphenyl)methyl]-1H-pyrazolo[3,4-b]pyridin-5-yl)phenylmethanone Part C compound (2.4 g, 6.6 mmol) was suspended in 10 mL of POCl$_3$ then heated to 108° C. for 1.5 h under nitrogen. The reaction mixture was cooled to 0° C. and diluted with CH$_2$Cl$_2$ (100 mL). Water (100 mL) was added slowly and the solution was basified to pH 8 with 5N aqueous NaOH solution. The organic layer was separated and the aqueous layer was extracted with CH$_2$Cl$_2$ (3×100 mL). The combined organic layers were dried (Na$_2$SO$_4$) and concentrated in vacuo to give a dark oil which was purified by flash chromatography (Merck silica, 230–400 mesh, loaded with CH$_2$Cl$_2$, eluted with 1:4 EtOAc/hexane) to give Part D compound (1.5 g, 60%) as a light yellow solid.

E. [4-(Cyclohexylmethoxy)-1-[(4-methoxyphenyl)methyl]-1H-pyrazolo[3,4-b]pyridin-5-yl]phenylmethanone To a solution of cyclohexylmethanol (0.050 mL, 0.41 mmol) and dry CH$_2$Cl$_2$ (10 mL, distilled from CaH$_2$) was added sodium hydride (16 mg, 0.40 mmol) in portions. The reaction mixture was stirred at room temperature for 15 minutes and then Part D compound (50 mg, 0.13 mmol) was added. After 6 h the reaction was diluted with water (10 mL) and the organic layer was separated. The aqueous layer was extracted with CH$_2$Cl$_2$ (3×10 mL). The combined organic layers were dried (Na$_2$SO$_4$) and concentrated in vacuo to give Part E compound as an oil which was used crude in the following reaction.

F. [4-(Cyclohexylmethoxy)-1H-pyrazolo[3,4-b]pyridin-5-yl]phenylmethanone

A mixture of crude Part E compound in TFA (2 mL) was heated at 65° C. for 2.5 h and then cooled to room temperature. The TFA was removed in vacuo and the remaining residue was dissolved in CH$_2$Cl$_2$ (10 mL) and saturated NaHCO$_3$ (10 mL) was added. The organic layer was separated and the aqueous layer was extracted with CH$_2$Cl$_2$ (3×10 mL). The combined organic layers were dried (Na$_2$SO$_4$) and concentrated in vacuo to give a crude oil which was purified by flash chromatography (Merck silica, 230–400 mesh, eluted with 1:19 MeOH/CH$_2$Cl$_2$) to afford the title compound (35 mg, 80% from Part D compound) as a white solid.

LC-MS: 336 (M+H)$^+$.

HPLC: $T_R$ (YMC S3 ODS 4.6×50 mm; 2.5 mL/min, gradient 0–100% B over 8 minutes, Buffer A=MeOH/H$_2$O/H$_3$PO$_4$ (10:90:0.2), Buffer B=MeOH/H$_2$O/H$_3$PO$_4$ (90:10:0.2))=7.7 minutes, >98% of total peak area at 254 nM.

EXAMPLE 5

[4-(Phenylmethoxy)-1H-pyrazolo[3,4-b]pyridin-5-yl]phenylmethanone

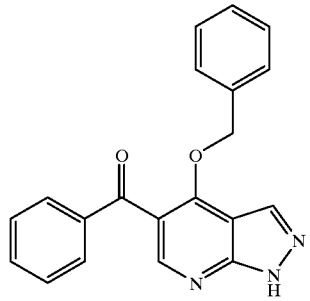

To a solution of [4-hydroxy-1H-pyrazolo[3,4-b]pyridin-5-yl]phenylmethanone (50 mg, 0.21 mmol) in methanol (1 mL) and saturated aqueous NaHCO$_3$ solution (10 mL) was added benzyl bromide (0.027 mL, 0.23 mmol). The reaction mixture was stirred at room temperature for 16 h and extracted with CH$_2$Cl$_2$ (3×10 mL). The combined organic layers were dried (Na$_2$SO$_4$) and concentrated in vacuo to give an oil. The crude material was purified by flash chromatography (SiO$_2$, 230–400 mesh, eluted with 1:19 MEOH/CH$_2$Cl$_2$) to afford the title compound (13 mg, 20%) as a white solid.

EXAMPLE 6

[4-(Butylthio)-1H-pyrazolo[3,4-b]pyridin-5-yl] phenylmethanone

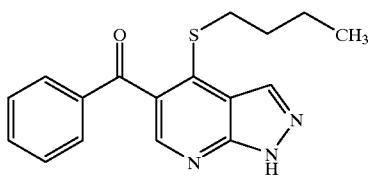

(4-(Butylthio)-1-[(4methoxyphenyl)methyl]-1H-pyrazolo[3.4-b]pyridin-5-yl)phenylmethanone To a solution of 1-butanethiol (0.085 mL, 0.79 mmol) in dry $CH_2Cl_2$ (10 mL, distilled from $CaH_2$) was added sodium hydride dispersion (60% in oil, 16 mg, 0.40 mmol) in portions. The reaction mixture was stirred at room temperature for 15 minutes and then Example 4, Part D compound (50 mg, 0.13 mmol) was added. After 6 h the reaction was diluted with water (10 mL) and the organic layer was separated. The aqueous layer was extracted with $CH_2Cl_2$ (3×10 mL). The combined organic layers were dried ($Na_2SO_4$) and concentrated in vacuo to give Part A compound as an oil which was used crude in the following reaction.

B. [4-(Butylthio)-1H-pyrazolo[3,4-b]pyridin-5-yl] phenylmethanone

Crude Part A compound was dissolved in TFA (2 mL) and the mixture was heated at 65° C. for 2.5 h, then cooled to room temperature. The TFA was removed in vacuo and the remaining residue was dissolved in $CH_2Cl_2$ (10 mL) and saturated aqueous $NaHCO_3$ (10 mL) was added. The organic layer was separated and the aqueous layer was extracted with $CH_2Cl_2$ (3×10 mL). The combined organic layers were dried ($Na_2SO_4$) and concentrated in vacuo to give a light yellow solid. The crude material was purified by flash chromatography ($SiO_2$, 230–400 mesh, eluted with 1:19 MeOH / $CH_2Cl_2$) to give the title compound (24 mg, 60%) as a white solid.

LC-MS: 312 (M+H)$^+$.

HPLC: $T_R$ (YMC S3 ODS 4.6×50 mm; 2.5 mL/min, gradient 0–100% B over 8 minutes, Buffer A=MeOH/$H_2O$/$H_3PO_4$ (10:90:0.2), Buffer B=MeOH/$H_2O$/$H_3PO_4$ (90:10:0.2))=7.7 minutes, >98% of total peak area at 254 nM.

EXAMPLE 7

[4-(Butylsulfinyl)-1H-pyrazolo[3,4-b]pyridin-5-yl] phenylmethanone

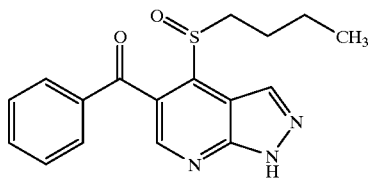

To Example 6 compound (10 mg, 0.032 mmol) in MeOH (1 ml) and $CH_2Cl_2$ (0.5 mL) cooled to 0° C. was added a solution of OXONE® (89 mg, 0.15 mmol) in $H_2O$ (1 mL). The reaction mixture was stirred at 0° C. for 15 h and water (10 mL) was added. The aqueous layer was extracted with $CH_2Cl_2$ (3×100 mL). The combined organic layers were dried ($Na_2SO_4$) and concentrated in vacuo to give yellow solid which was purified by flash chromatography ($SiO_2$, 230–400 mesh, loaded with $CH_2Cl_2$, eluted with 1:19 MeOH/$CH_2Cl_2$ to give the title compound (6 mg, 60%) as a yellow solid.

LC-MS: 328 (M+H)$^+$.

HPLC: $T_R$ (YMC S3 ODS 4.6×50 mm; 2.5 mL/min, gradient 0–100% B over 8 minutes, Buffer A=MeOH/$H_2O$/$H_3PO_4$ (10:90:0.2), Buffer B=MeOH/$H_2O$/$H_3PO_4$ (90:10:0.2))=7.1 minutes, >98% of total peak area at 254 nM.

EXAMPLE 8

[4(Butylsulfonyl)-1H-pyrazolo[3,4-b]pyridin-5-yl] phenylmethanone

To Example 6 compound (10 mg, 0.032 mmol) in $CH_2Cl_2$ (10 mL) was added at room temperature m-chloroperoxybenzoic acid (22 mg, 0.13 mmol). The reaction mixture was stirred at room temperature for 1.5 h and then quenched by addition of saturated aqueous $NaHCO_3$ (10 mL). The organic layer was separated and the aqueous layer was extracted with $CH_2Cl_2$ (3×100 mL). The combined organic layers were dried ($Na_2SO_4$) and concentrated in vacuo to give a yellow solid which was purified by flash chromatography ($SiO_2$, 230–400 mesh, loaded with $CH_2Cl_2$, eluted with 1:1 EtOAc/hexane) to give the title compound (5 mg, 50%) as a yellow solid.

LC-MS: 344 (M+H)$^+$.

HPLC: $T_R$ (YMC S3 ODS 4.6×50 mm; 2.5 mL/min, gradient 0–100% B over 8 minutes, Buffer A=MeOH/$H_2O$/$H_3PO_4$ (10:90:0.2), Buffer B=MeOH/$H_2O$/$H_3PO_4$ (90:10:0.2))=6.7 minutes, >98% of total peak area at 254 nM.

What is claimed is:

1. A method for inhibiting cyclin dependent kinases, which comprises administering to a mammalian specie in need thereof, an effective cyclin dependent kinase inhibiting amount of a compound of the formula (I)

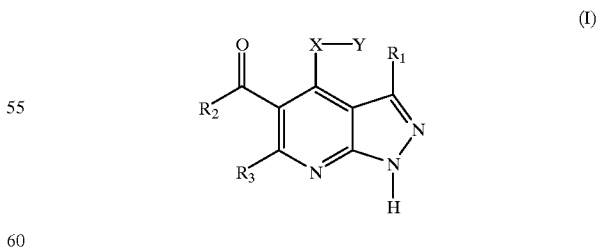

or pharmaceutically acceptable salts thereof wherein:
X is oxygen;
Y is lower alkyl;
$R_1$ is hydrogen;
$R_2$ is aryl; and
$R_3$ is hydrogen.

2. A compound selected from (4-Butoxy-1H-pyrazolo[3,4-b]pyridin-5-yl)(2,4,6-trifluorophenyl) methanone;

(4-Butoxy-1H-pyrazolo[3,4-b]pyridin-5-yl)(2,3,5,6-tetrafluoro-4-methylphenyl)methanone;

4-Butoxy-N-(2-methylpropyl)-1H-pyrazolo[3,4-b]pyridine-5-carboxamide;

[4-(Cyclohexylmethoxy)-1H-pyrazolo[3,4-b]pyridin-5-yl]phenylmethanone;

[4-(Phenylmethoxy)-1H-pyrazolo[3,4-b]pyridin-5-yl]phenylmethanone;

[4-(Butylthio)-1H-pyrazolo[3,4-b]pyridin-5-yl]phenylmethanone;

[4-(Butylsulfinyl)-1H-pyrazolo[3,4-b]pyridin-5-yl]phenylmethanone; and

[4-(Butylsulfonyl)-1H-pyrazolo[3,4-b]pyridin-5-yl]phenylmethanone; or a pharmaceutically acceptable salt thereof.

3. The method as recited in claim 1, which comprises the administration of a pharmaceutical composition comprising a compound of formula (I) and a pharmaceutically acceptable carrier.

4. A method for inhibiting cyclin dependent kinases, which comprises the administration of a pharmaceutical composition comprising a compound of formula (I)

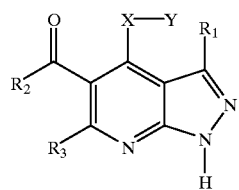

(I)

or a pharmaceutically acceptable salt thereof wherein:

X is O or $S(O)_m$;

Y is alkyl, aryl, arylalkyl, heteroaryl, heteroarylalkyl, cycloalkyl, cycloalkylalkyl, heterocycloalkyl or heterocycloalkylalkyl;

$R_1$ is hydrogen or lower alkyl;

$R_2$ is alkyl, aryl, arylalkyl, heteroaryl, heteroarylalkyl, cycloalkyl, cycloalkylalkyl, heterocycloalkyl, heterocycloalkylalkyl, —O-alkyl, —O-aryl or —$NR_4R_5$;

$R_3$ is hydrogen or lower alkyl;

$R_4$ is hydrogen, alkyl, aryl, arylalkyl, heteroaryl, heteroarylalkyl, cycloalkyl, cycloalkylalkyl, heterocycloalkyl, heterocycloalkylalkyl, —O-alkyl or —O-aryl;

$R_5$ is hydrogen, alkyl, aryl, alkylaryl, heteroaryl, alkylheteroaryl, cycloalkyl, alkylcycloalkyl, heterocycloalkyl, alkylheterocycloalkyl, —O-alkyl or —O-aryl; and m is 0, 1 or 2 administered in combination with a pharmaceutically acceptable carrier, with an anticancer treatment or anticancer agent administered in sequence.

5. The method as recited in claim 4, wherein said combination comprising said compound of formula (I) and said pharmaceutically acceptable carrier, is administered prior to administration of said anticancer treatment or anticancer agent.

6. The method as recited in claim 4, wherein said combination comprising said compound of formula (I) and said pharmaceutically acceptable carrier, is administered after administration of said anticancer treatment or anticancer agent.

7. A method for treating infection by HIV, or for treating and preventing the development of AIDS, comprising administering to a mammalian specie in need thereof a therapeutically effective amount of a composition comprising a pharmaceutically acceptable carrier and a compound of formula (I)

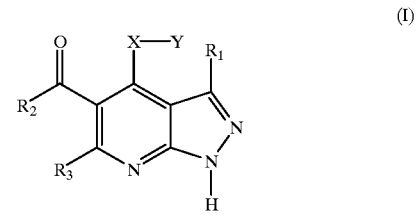

(I)

or a pharmaceutically acceptable salt thereof wherein:

X is O or $S(O)_m$;

Y is alkyl, aryl, arylalkyl, heteroaryl, heteroarylalkyl, cycloalkyl, cycloalkylalkyl, heterocycloalkyl or heterocycloalkylalkyl;

$R_1$ is hydrogen or lower alkyl;

$R_2$ is alkyl, aryl, arylalkyl, heteroaryl, heteroarylalkyl, cycloalkyl, cycloalkylalkyl, heterocycloalkyl, heterocycloalkylalkyl, —O-alkyl, —O-aryl or —$NR_4R_5$;

$R_3$ is hydrogen or lower alkyl;

$R_4$ is hydrogen, alkyl, aryl, arylalkyl, heteroaryl, heteroarylalkyl, cycloalkyl, cycloalkylalkyl, heterocycloalkyl, heterocycloalkylalkyl, —O-alkyl or —O-aryl;

$R_5$ is hydrogen, alkyl, aryl, alkylaryl, heteroaryl, alkylheteroaryl, cycloalkyl, alkylcycloalkyl, heterocycloalkyl, alkylheterocycloalkyl, —O-alkyl or —O-aryl; and m is 0, 1 or 2.

8. A method for treating viral infections, comprising administering to a mammalian specie in need thereof a therapeutically effective amount of a composition comprising a pharmaceutically acceptable carrier and a compound of formula (I)

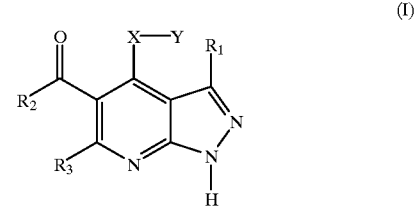

(I)

or a pharmaceutically acceptable salt thereof wherein:

X is O or $S(O)_m$;

Y is alkyl, aryl, arylalkyl, heteroaryl, heteroarylalkyl, cycloalkyl, cycloalkylalkyl, heterocycloalkyl or heterocycloalkylalkyl;

$R_1$ is hydrogen or lower alkyl;

$R_2$ is alkyl, aryl, arylalkyl, heteroaryl, heteroarylalkyl, cycloalkyl, cycloalkylalkyl, heterocycloalkyl, heterocycloalkylalkyl, —O-alkyl, —O-aryl or —$NR_4R_5$;

$R_3$ is hydrogen or lower alkyl;

$R_4$ is hydrogen, alkyl, aryl, arylalkyl, heteroaryl, heteroarylalkyl, cycloalkyl, cycloalkylalkyl, heterocycloalkyl, heterocycloalkylalkyl, —O-alkyl or —O-aryl;

$R_5$ is hydrogen, alkyl, aryl, alkylaryl, heteroaryl, alkylheteroaryl, cycloalkyl, alkylcycloalkyl, heterocycloalkyl, alkylheterocycloalkyl, —O-alkyl or —O-aryl; and m is 0, 1 or 2.

9. A method for treating fungal infections, comprising administering to a mammalian specie in need thereof a therapeutically effective amount of a composition comprising a pharmaceutically acceptable carrier and a compound of formula (I)

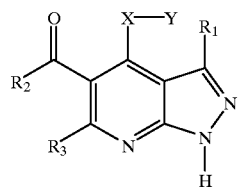
(I)

or a pharmaceutically acceptable salt thereof wherein:

X is O or $S(O)_m$;

Y is alkyl, aryl, arylalkyl, heteroaryl, heteroaryalkyl, cycloalkyl, cycloalkylalkyl, heterocycloalkyl or heterocycloalkylalkyl;

$R_1$ is hydrogen or lower alkyl;

$R_2$ is alkyl, aryl, arylalkyl, heteroaryl, heteroarylalkyl, cycloalkyl, cycloalkylalkyl, heterocycioalkyl, heterocycloalkylalkyl, —O-alkyl, —O-aryl or —$NR_4R_5$;

$R_3$ is hydrogen or lower alkyl;

$R_4$ is hydrogen, alkyl, aryl, arylalkyl, heteroaryl, heteroarylalkyl, cycloalkyl, cycloalkylalkyl, heterocycloalkyl, heterocycloalkylalkyl, —O-alkyl or —O-aryl;

$R_5$ is hydrogen, alkyl, aryl, alkylaryl, heteroaryl, alkylheteroaryl, cycloalkyl, alkylcycloalkyl, heterocycloalkyl, alkylheterocycloalkyl, —O-alkyl or —O-aryl; and m is 0, 1 or 2.

10. A method for preventing the development of cancer or tumor relapse, comprising administering to a mammalian specie in need thereof a therapeutically effective amount of a composition comprising a pharmaceutically acceptable carrier and a compound of formula (I)

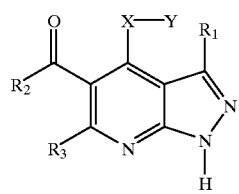
(I)

or a pharmaceutically acceptable salt thereof wherein:

X is O or $S(O)_m$;

Y is alkyl, aryl, arylalkyl, heteroaryl, heteroarylalkyl, cycloalkyl, cycloalkylalkyl, heterocycloalkyl or heterocycloalkylalkyl;

$R_1$ is hydrogen or lower alkyl;

$R_2$ is alkyl, aryl, arylalkyl, heteroaryl, heteroarylalkyl, cycloalkyl, cycloalkylalkyl, heterocycloalkyl, heterocycloalkylalkyl, —O-alkyl, —O-aryl or —$NR_4R_5$;

$R_3$ is hydrogen or lower alkyl;

$R_4$ is hydrogen, alkyl, aryl, arylalkyl, heteroaryl, heteroarylalkyl, cycloalkyl, cycloalkylalkyl, heterocycloalkyl, heterocycloalkylalkyl, —O-alkyl or —O-aryl;

$R_5$ is hydrogen, alkyl, aryl, alkylaryl, heteroaryl, alkylheteroaryl, cycloalkyl, alkylcycloalkyl, heterocycloalkyl, alkylheterocycloalkyl. —O-alkyl or —O-aryl; and m is 0, 1 or 2.

11. A method for treating neurodegenerative disease, comprising administering to a mammalian specie in need thereof a therapeutically effective amount of a composition comprising a pharmaceutically acceptable carrier and a compound of formula (I)

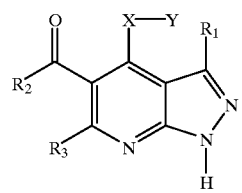
(I)

or a pharmaceutically acceptable salt thereof wherein:

X is O or $S(O)_m$;

Y is alkyl, aryl, arylalkyl, heteroaryl, heteroarylalkyl, cycloalkyl, cycloalkylalkyl, heterocycloalkyl or heterocycloalkylalkyl;

$R_1$ is hydrogen or lower alkyl;

$R_2$ is alkyl, aryl, arylalkyl, heteroaryl, heteroarylalkyl, cycloalkyl, cycloalkylalkyl, heterocycloalkyl, heterocycloalkylalkyl, —O-alkyl, —O-aryl or —$NR_4R_5$;

$R_3$ is hydrogen or lower alkyl;

$R_4$ is hydrogen, alkyl, aryl, arylalkyl, heteroaryl, heteroarylalkyl, cycloalkyl, cycloalkylalkyl, heterocycloalkyl, heterocycloalkylalkyl, —O-alkyl or —O-aryl;

$R_5$ is hydrogen, alkyl, aryl, alkylaryl, heteroaryl, alkylheteroaryl, cycloalkyl, alkylcycloalkyl, heterocycloalkyl, alkylheterocycloalkyl, —O-alkyl or —O-aryl; and m is 0, 1 or 2.

12. A method for preventing the development of cancer or tumor relapse, comprising administering to a mammalian specie in need thereof a therapeutically effective amount of a composition comprising a compound of the formula

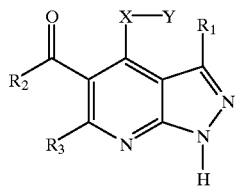

(I)

or a pharmaceutically acceptable salt thereof wherein:

X is O or S(O)$_m$;

Y is alkyl, aryl, arylalkyl, heteroaryl, heteroarylalkyl, cycloalkyl, cycloalkylalkyl, heterocycloalkyl or heterocycloalkylalkyl;

$R_1$ is hydrogen or lower alkyl;

$R_2$ is alkyl, aryl, arylalkyl, heteroaryl, heteroarylalkyl, cycloalkyl, cycloalkylalkyl, heterocycloalkyl, heterocycloalkylalkyl, —O-alkyl, —O-aryl or —NR$_4$R$_5$;

$R_3$ is hydrogen or lower alkyl;

$R_4$ is hydrogen, alkyl, aryl, arylalkyl, heteroaryl, heteroarylalkyl, cycloalkyl, cycloalkylalkyl, heterocycloalkyl, heterocycloalkylalkyl, —O-alkyl or —O-aryl;

$R_5$ is hydrogen, alkyl, aryl, alkylaryl, heteroaryl, alkylheteroaryl, cycloalkyl, alkylcycloalkyl, heterocycloalkyl, alkylheterocycloalkyl, —O-alkyl or —O-aryl; and m is 0, 1 or 2;

in combination with a pharmaceutically acceptable carrier, and an anti-cancer agent formulated in a fixed dose.

13. A method for treating cancer comprising administering to a mammalian specie in need thereof a therapeutically effective amount of a composition comprising a compound of the formula

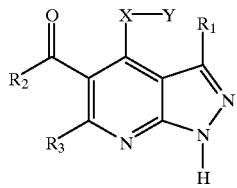

(I)

or a pharmaceutically acceptable salt thereof wherein:

X is O or S(O)$_m$;

Y is alkyl, aryl, arylalkyl, heteroaryl, heteroarylalkyl, cycloalkyl, cycloalkylalkyl, heterocycloalkyl or heterocycloalkylalkyl;

$R_1$ is hydrogen or lower alkyl;

$R_2$ is alkyl, aryl, arylalkyl, heteroaryl, heteroarylalkyl, cycloalkyl, cycloalkylalkyl, heterocycloalkyl, heterocycloalkylalkyl, —O-alkyl, —O-aryl or —NR$_4$R$_5$;

$R_3$ is hydrogen or lower alkyl;

$R_4$ is hydrogen, alkyl, aryl, arylalkyl, heteroaryl, heteroarylalkyl, cycloalkyl, cycloalkylalkyl, heterocycloalkyl, heterocycloalkylalkyl, —O-alkyl or —O-aryl;

$R_5$ is hydrogen, alkyl, aryl, alkylaryl, heteroaryl, alkylheteroaryl, cycloalkyl, alkylcycloalkyl, heterocycloalkyl, alkylheterocycloalkyl, —O-alkyl or —O-aryl; and m is 0, 1 or 2;

in combination with a pharmaceutically acceptable carrier, with an anti-cancer treatment or anti-cancer agent administered in sequence.

14. A method for preventing the development of cancer or tumor relapse, comprising administering to a mammalian specie in need thereof a therapeutically effective amount of a composition comprising a compound of the formula

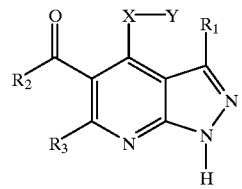

(I)

or a pharmaceutically acceptable salt thereof wherein:

X is O or S(O)$_m$;

Y is alkyl, aryl, arylalkyl, heteroaryl, heteroarylalkyl, cycloalkyl, cycloalkylalkyl, heterocycloalkyl or heterocycloalkylalkyl;

$R_1$ is hydrogen or lower alkyl;

$R_2$ is alkyl, aryl, arylalkyl, heteroaryl, heteroarylalkyl, cycloalkyl, cycloalkylalkyl, heterocycloalkyl, heterocycloalkylalkyl, —O-alkyl, —O-aryl or —NR$_4$R$_5$;

$R_3$ is hydrogen or lower alkyl;

$R_4$ is hydrogen, alkyl, aryl, arylalkyl, heteroaryl, heteroarylalkyl, cycloalkyl, cycloalkylalkyl, heterocycloalkyl, heterocycloalkylalkyl, —O-alkyl or —O-aryl;

$R_5$ is hydrogen, alkyl, aryl, alkylaryl, heteroaryl, alkylheteroaryl, cycloalkyl, alkylcycloalkyl, heterocycloalkyl, alkylheterocycloalkyl, —O-alkyl or —O-aryl; and m is 0, 1 or 2;

in combination with a pharmaceutically acceptable carrier, with an anti-cancer treatment or anti-cancer agent administered in sequence.

15. A method for inhibiting cyclin dependent kinases, which comprises administering to a mammalian specie in need thereof, an effective cyclin dependent kinase inhibiting amount of a compound of the formula

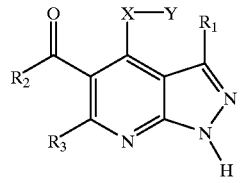

(I)

or pharmaceutically acceptable salts thereof wherein:

X is oxygen;

Y is lower alkyl;

$R_1$ is hydrogen;

$R_2$ is 4-bromo-2,6-difluorophenyl, 4-chloro-2,6-difluorophenyl, or 2,4,6-trifluorophenyl; and $R_3$ is hydrogen.

16. A method for inhibiting cyclin dependent kinases, which comprises administering to a mammalian specie in need thereof, an effective cyclin dependent kinase inhibiting amount of a compound of the formula

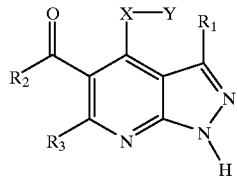
(I)

or pharmaceutically acceptable salts thereof wherein:
X is $S(O)_m$;
Y is lower alkyl;
$R_1$ is hydrogen;
$R_2$ is 4-bromo-2,6-difluorophenyl, 4-chloro-2,6-difluorophenyl, or 2,4,6-trifluorophenyl;
$R_3$ is hydrogen; and
m is 0.

17. A method for inhibiting cyclin dependent kinases, which comprises administering to a mammalian specie in need thereof, an effective cyclin dependent kinase inhibiting amount of a compound of the formula

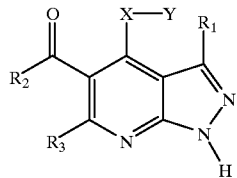
(I)

or pharmaceutically acceptable salts thereof wherein:
X is $S(O)_m$;
Y is lower alkyl;
$R_1$ is hydrogen;
$R_2$ is 4-bromo-2,6-difluorophenyl, 4-chloro-2,6-difluorophenyl, or 2,4,6-trifluorophenyl;
$R_3$ is hydrogen; and
m is 1 or 2.

18. A method for inhibiting cyclin dependent kinases, which comprises the administration of a pharmaceutical composition comprising a compound of the formula

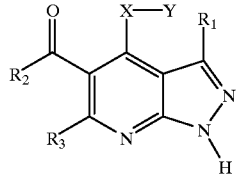
(I)

or pharmaceutically acceptable salts thereof, wherein:
X is O, $S(O)_m$;
Y is alkyl, aryl, arylalkyl, heteroaryl, heteroarylalkyl, cycloalkyl, cycloalkylalkyl, heterocycloalkyl, heterocycloalkylalkyl;
$R_1$ is hydrogen or lower alkyl;
$R_2$ is alkyl, aryl, arylalkyl, heteroaryl, heteroarylalkyl, cycloalkyl, cycloalkylalkyl, heterocycloalkyl, heterocycloalkylalkyl, —O-alkyl, —O-aryl, —NR$_4$R$_5$;
$R_3$ is hydrogen or lower alkyl;
$R_4$ is hydrogen, alkyl, aryl, arylalkyl, heteroaryl, heteroarylalkyl, cycloalkyl, cycloalkylalkyl, heterocycloalkyl, heterocycloalkylalkyl, —O-alkyl, —O-aryl;
$R_5$ is hydrogen, alkyl, aryl, alkylaryl, heteroaryl, alkylheteroaryl, cycloalkyl, alkylcycloalkyl, heterocycloalkyl, alkylheterocycloalkyl, —O-alkyl, —O-aryl; and
m is 0, 1 or 2;
in combination with a pharmaceutically acceptable carrier, and an anti-cancer agent formulated in a fixed dose.

19. A method for treating cancer, which comprises administering to a mammalian specie in need thereof, a therapeutically effective amount of a pharmaceutical composition comprising a compound of the formula

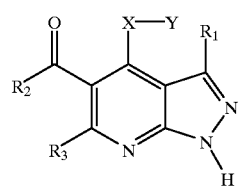
(I)

or pharmaceutically acceptable salts thereof, wherein:
X is O, $S(O)_m$;
Y is alkyl, aryl, arylalkyl, heteroaryl, heteroarylalkyl, cycloalkyl, cycloalkylalkyl, heterocycloalkyl, heterocycloalkylalkyl;
$R_1$ is hydrogen or lower alkyl;
$R_2$ is alkyl, aryl, arylalkyl, heteroaryl, heteroarylalkyl, cycloalkyl, cycloalkylalkyl, heterocycloalkyl, heterocycloalkylalkyl, —O-alkyl, —O-aryl, —NR$_4$R$_5$;
$R_3$ is hydrogen or lower alkyl;
$R_4$ is hydrogen, alkyl, aryl, arylalkyl, heteroaryl, heteroarylalkyl, cycloalkyl, cycloalkylalkyl, heterocycloalkyl, heterocycloalkylalkyl, —O-alkyl, —O-aryl;
$R_5$ is hydrogen, alkyl, aryl, alkylaryl, heteroaryl, alkylheteroaryl, cycloalkyl, alkylcycloalkyl, heterocycloalkyl, alkylheterocycloalkyl, —O-alkyl, —O-aryl; and
m is 0, 1 or 2;
in combination with a pharmaceutically acceptable carrier, and an anti-cancer agent formulated in a fixed dose.

20. The method as recited in claim 15, which comprises the administration of a pharmaceutical composition comprising a compound of formula (I) and a pharmaceutically acceptable carrier.

21. The method as recited in claim 16, which comprises the administration of a pharmaceutical composition comprising a compound of formula (I) and a pharmaceutically acceptable carrier.

22. The method as recited in claim 17, which comprises the administration of a pharmaceutical composition comprising a compound of formula (I) and a pharmaceutically acceptable carrier.

23. The method according to claim 1, which comprises inhibiting a cyclin dependent kinase selected from the group consisting of cdk1, cdk2, cdk3, cdk4, cdk5, cdk6, cdk7 and cdk8.

24. The method according to claim 15, which comprises inhibiting a cyclin dependent kinase selected from the group consisting of cdk1, cdk2, cdk3, cdk4, cdk5, cdk6, cdk7 and cdk8.

25. The method according to claim 16, which comprises inhibiting a cyclin dependent kinase selected from the group consisting of cdk1, cdk2, cdk3, cdk4, cdk5, cdk6, cdk7 and cdk8.

26. The method according to claim 17, which comprises inhibiting a cyclin dependent kinase selected from the group consisting of cdk1, cdk2, cdk3, cdk4, cdk5, cdk6, cdk7 and cdk8.

* * * * *